United States Patent [19]

Bailey

[11] Patent Number: 4,525,876
[45] Date of Patent: Jul. 2, 1985

[54] WELDER'S HELMET

[76] Inventor: Bernard A. Bailey, Box 306, Deer Lodge, Mont. 59722

[21] Appl. No.: 442,894

[22] Filed: Nov. 19, 1982

Related U.S. Application Data

[63] Continuation-in-part of Ser. No. 202,646, Oct. 31, 1980, abandoned.

[51] Int. Cl.³ .............................................. A61F 9/06
[52] U.S. Cl. .......................................................... 2/8
[58] Field of Search ................. 2/8, 11, 427, 431, 432, 2/438, 424, 9

[56] References Cited

U.S. PATENT DOCUMENTS

| | | | |
|---|---|---|---|
| 2,386,656 | 10/1945 | Carlson | 2/8 |
| 2,416,764 | 3/1947 | Madson | 2/8 |
| 3,095,575 | 7/1963 | Radov | 2/8 |
| 3,775,774 | 12/1973 | Herman | 2/8 |

Primary Examiner—Peter Nerbun
Attorney, Agent, or Firm—Arthur L. Urban

[57] ABSTRACT

A welder's helmet including a helmet portion, a filter support portion, a filter portion and a filter actuating portion; the helmet portion including a shield section, a head band section connected to the shield section, a viewing opening in the shield section; the filter support portion being mounted adjacent to the viewing opening, the filter support portion including a first frame section disposed over the outside of the viewing opening, second and third frame sections disposed over the inside of the viewing opening, the second and third frame sections each including an opening therein adjacent to the shield viewing opening; the filter portion including a filter member slidably positioned between the second and third frame sections and movable from a position between the second and third frame section openings to a position below same; the filter actuating portion including an actuator plate section disposed over the third frame section and movable with respect thereto, an actuator arm member disposed between the second and third frame sections, the actuator arm member being pivotally connected to one of the second or third frame sections, the pivotal connection being adjacent one end of the arm member, a link member operatively connecting the filter member with the actuator arm member at a point remote from the pivotally connected end thereof, the actuator arm member being operatively connected to the actuator plate section, biasing mechanism urging the filter member into a position over the viewing opening of the shield section, a chin-contacting member affixed to the actuator plate section and including substantially horizontal and vertical sections.

12 Claims, 5 Drawing Figures

WELDER'S HELMET

This application is a continuation-in-part of pending application Ser. No. 202,646, filed Oct. 31, 1980, now abandoned.

This invention relates to a novel welder's helmet and more particularly relates to a welder's helmet with a movable filter.

Welders use shields over their faces to protect themselves from flying sparks and hot fragments of metal. In order to see their work they are welding, it is necessary for the shield to have a viewing port. This viewing port generally is covered with a filter to screen out the harmful rays being emitted from the welding flame or light.

While the use of welding shields with filters allows a welder to view the welding operation safely, the density or darkness of the filter prevents the welder from being able to view areas which are less intensely lighted. To provide such additional viewability, the welder is faced with alternatives which represent compromises rather than a desired solution.

A welder can utilize a shield with a filter having a lower density. However, a less dense filter can present a hazard to a welder's vision, particularly if he spends considerable time at his work. Another alternative is to employ a pivoting hood that can be moved away from the face. Raising and lowering the hood can be an annoyance if a welder is working full time. Also, this type of hood can present a safety hazard if the welder fails to lower the hood quickly enough when he begins welding or if he forgets to lower the hood.

To avoid creating a safety hazard, a welder must direct at least a portion of his attention to the positioning of the hood. Otherwise, he may injure his face and/or eyes. Another problem with pivoting hoods is that they require the use of a hand to change the position of the hood. A welder must have one of his hands free which may require him to lay down the work or the welding torch, change the hood and then pick up what he needs. In any case, his efficiency and production will be less than he could achieve without the interference and inconvenience encountered with pivoting hoods.

In an attempt to overcome the above problem it has been proposed in U.S. Pat. No. 3,095,575 to utilize a fixed hood with a pair of lenses, one of which is movable. The movable lens is moved with a mechanism that is actuated by chin movement of the person wearing the hood. The chin-actuated mechanism as described in the patent has a flat chin plate positioned at the end of a bracket. The opposite end of the bracket is pivotally connected to a slide member affixed to the movable lens. A longitudinal screw provides for adjustment of the position of the chin plate and bracket with respect to the slide member.

The chin-actuated mechanism also includes a floating coil or torsion spring, the ends of which are hooked over lugs operatively connected to a frame supporting the movable lens. When the chin plate is depressed, the bracket and slide member linkage overcomes the force of the spring to lower the lens and provide visibility of areas with lower intensity of light. When the wearer wishes to view the welding operation, he simply raises his chin so that the spring will raise the movable lens to a point adjacent the fixed lens and thus provide a maximum filtering effect.

The utilization of a chin-actuated mechanism to provide changes in the filtering effect of the lenses of a welder's hood in theory appears to provide an ideal solution to the problem of achieving good visibility while affording him a high degree of safety of his vision. However, in practice, the use of such a chin-actuated mechanism for changing the visibility through a lens of a welder's hood is not without its problems.

For example, the welder's hood described in the above patent may present problems in use. An individual may find it difficult to move his chin so that the position of the movable lens will be changed. With practice, users may develop the proper chin movement to effect movement of the lens. However, this may be a time-consuming task that can continue for a considerable period of time.

Also, if the hood is dropped or jarred, the spring or other component may become dislodged so that the mechanism will not function. Then it is necessary to disassemble the mechanism to reposition the parts and again reassemble the mechanism.

The disassembling of the mechanism not only takes considerable time but also takes time away from welding and thus reduces overall efficiency. Furthermore, the dislodging of the component may occur at a most inconvenient time such as when a rush job must be completed. In addition, the dislodging of the component probably will only be discovered as the hood is being used again when production time is limited.

The present invention provides a novel welder's helmet that overcomes the deficiencies of the hoods previously available. The helmet of the invention permits a welder to effect movement of a lens more easily. The design of the welding helmet of the invention enables an individual to learn more quickly how to operate the chin-actuating mechanism. The helmet permits more natural chin movement on the part of the user and thus can be used after a short conditioning period with a minimum of attention by the user.

The welder's helmet of the present invention is simple in design and relatively inexpensive. The helmet can be fabricated with commercially available components and materials. The helmet can be manufactured with conventional fabricating techniques using semi-skilled labor. Assembly of the helmet can be accomplished quickly and conveniently.

The helmet of the invention is durable in construction and has a long useful life. The helmet requires little maintenace so downtime is minimized. The helmet can be used by individuals of different head sizes and facial configurations.

Other benefits and advantages of the novel welder's helmet of the present invention will be apparent from the following description and the accompanying drawings in which.

Figure 1:
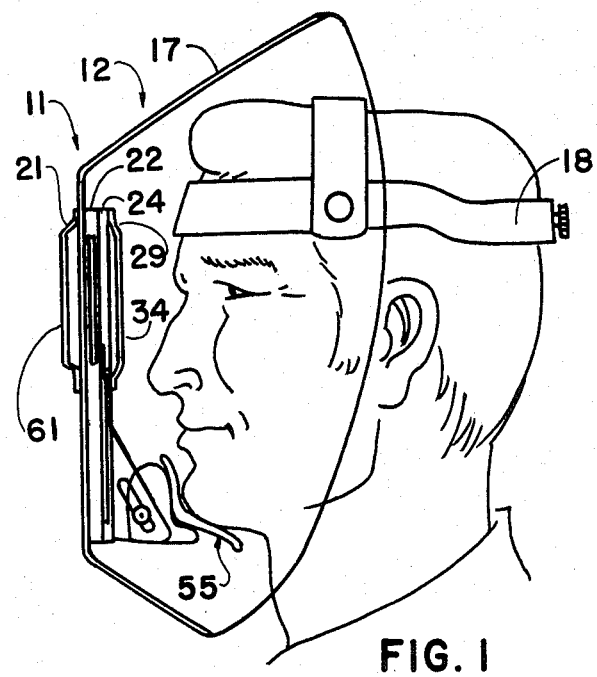
FIG. 1 is a side elevation in section of one form of the welder's helmet of the invention.

As shown in the drawings, one form of the novel welder's helmet 11 of the present invention is positioned on the head of a person and covers the face of the user.

The helmet 11 includes a helmet portion 12, a filter support portion 13, a filter portion 14 and a filter actuating portion 15.

The helmet portion 12 of the welder's helmet 11 of the invention includes a shield section 17. A head band section 18 is connected to the shield section 17. Advantageously, the head band section 18 is pivotally connected to the shield section. A viewing opening 19 is located in the shield section 17 at a point adjacent the eyes of the user. The viewing opening 19 preferably has a generally rectangular configuration with the larger dimension in a horizontal orientation.

The filter support portion 13 of the helmet of the invention is mounted adjacent to the viewing opening 19 of the shield section 17. The filter support portion 13 includes a first frame section 21. The first frame section is disposed over the outside of the viewing opening 19, that is, on the side of the shield section remote from the user's face. The filter support portion 13 advantageously includes a safety lens disposed on the outside of the viewing opening 19 in association with the first frame section 21.

The filter support portion 13 also includes a second frame section 22 which is disposed over the inside of the shield viewing opening 19. The second frame section 22 includes an opening 23 therein adjacent to the viewing opening 19 of the shield 17.

A third frame section 24 is disposed adjacent to the second frame section 22. The third frame section 24 also includes an opening 25 adjacent to the viewing opening 19. The third frame section 24 further includes an elongated vertically oriented slot 27 therethrough. Preferably, a pair of spaced slots 27 and 28 are located in the third frame section 24. The slot or slots are located below the opening 25 in the third frame section.

The filter support portion 13 advantageously includes a fourth frame section 29. The fourth frame section 29 is disposed over the third frame section 24. The various frame sections 21, 22, 24 and 29 are secured together preferably with a plurality of spaced fasteners such as studs 30 and nuts 31 affixed to the ends thereof.

The filter portion 14 of the welder's helmet 11 of the invention includes a filter member 33. The filter member 33 is slidably positioned between the second and third frame sections 22 and 24. The filter member 33 is movable from a position between the openings 23 and 25 of the second and third frame sections respectively to a position below the openings 23 and 25. At least one of the second or third frame sections 22 or 24 advantageously includes guide means 35 for the filter member 33.

In a preferred form of the helmet of the invention, the filter portion 14 includes more than one filter member such as filters 33 and 34 as shown in the drawings. Filter 33 may be movable while filter 34 is fixed. The use of a combination of filters provides protection for the user's eyes under a variety of different working conditions.

The filter actuating portion 15 of the helmet 11 of the invention includes an actuator plate section 36.

The actuator plate section 36 is disposed over the third frame section 24 and movable with respect thereto. The third frame section 24 and/or the fourth frame section 29, if it is present, advantageously includes guide means 39 for the actuator plate section 36. The actuator plate section is movable linearly in a plane substantially parallel to the third frame section.

The filter actuating portion further includes a stud member 37 and preferably a pair of spaced stud members 37 and 38. The stud members 37 and 38 are positioned on the plate section 36 and extend from one side thereof through the elongated openings 27 and 28 in the third frame section 24.

The filter actuating portion 15 also includes an actuator arm member 41. The actuator arm member 41 is disposed between the second and third frame sections 22 and 24. The actuator arm member 41 is pivotally connected to one of the second or third frame sections. The pivotal connection is adjacent one end 42 of the arm member.

A link member 43 operatively connects the filter member 33 with the actuator arm member 41. The connection thereof is at a point 44 remote from the pivotally connected end 42 thereof.

The actuator arm member 41 is operatively connected to the stud member 37 of the actuator plate section 36. Advantageously, the stud member 37 extends through an opening 45 disposed along the length of the actuator arm member 41.

Biasing means 47 urges the filter member 33 into a position over the viewing opening 19 of the shield section 17. The biasing means preferably includes a spring strip 48 operatively connected between the actuator plate section 36 and one of the frame sections.

As shown, one end 49 of the spring strip 48 advantageously bears against stud member 38 of plate section 36 that extends through opening 28 of the third frame section 24. The opposite end 51 of strip 48 bears against a stud 52 of the third frame section with the central part thereof resting on another stud 53.

The filter actuating portion 15 further includes a chin-contacting member 55 that is affixed to the actuator plate section 36. The chin-contacting member 55 includes a substantially horizontal section 56 and a substantially vertical section 57. The chin-contacting member 55 preferably is connected to the actuator plate section 36 through a triangular section 58. The triangular section 58 extends outwardly from the plate section substantially perpendicular thereto.

Figure 2:
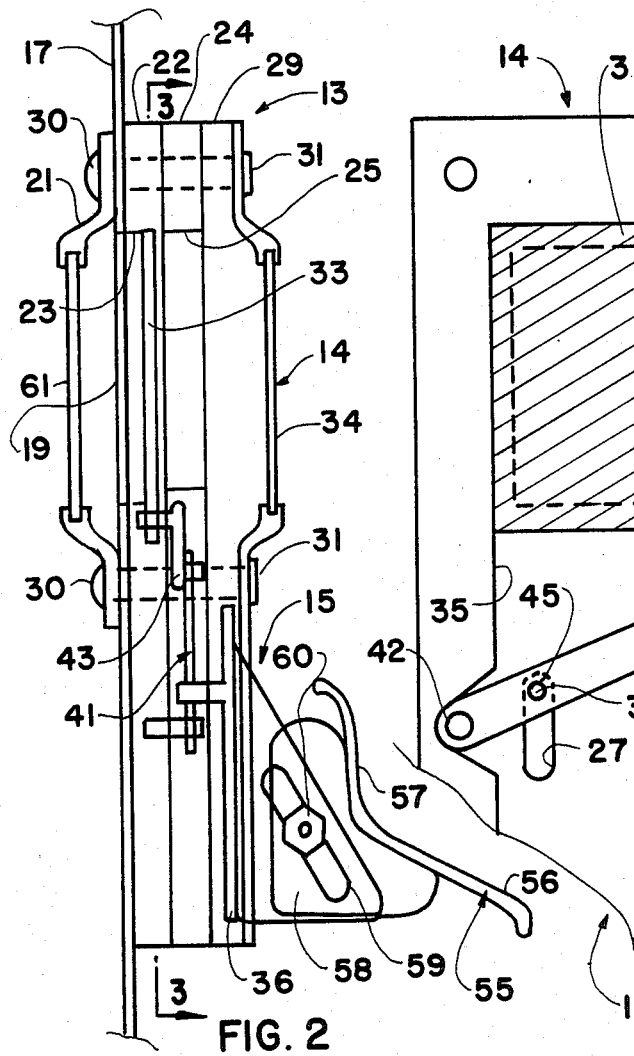
FIG. 2 is an enlarged fragmentary side view in section of the helmet shown in FIG. 1.
Figure 3:
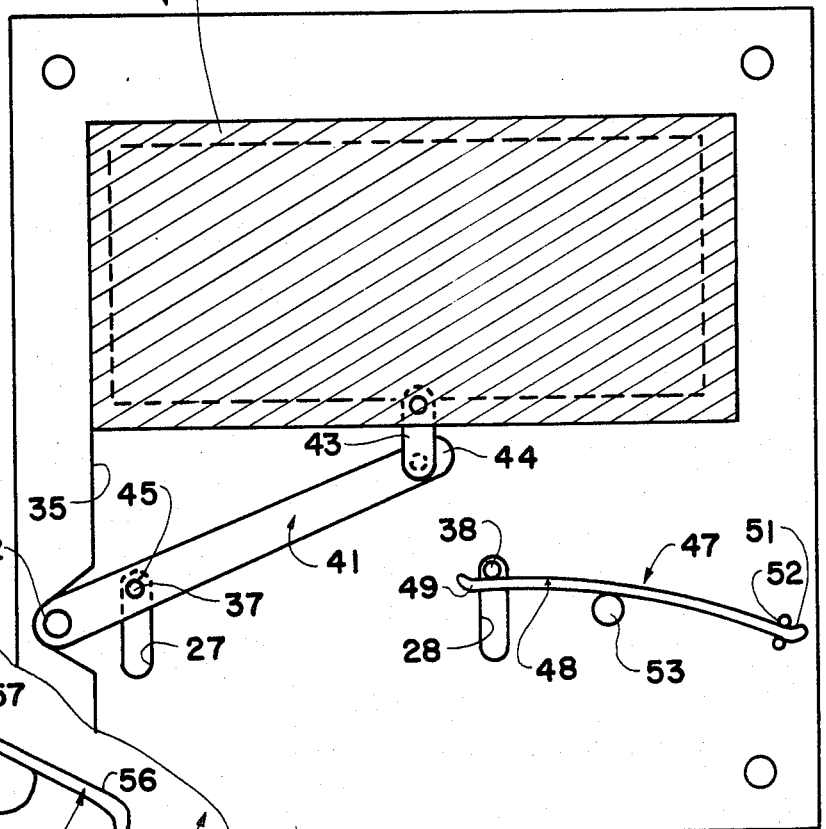
FIG. 3 is a fragmentary sectional view of the filter mechanism of the welder's helmet taken along line 3—3 of FIG. 2.

Advantageously, means are provided for adjusting the position of the chin-contacting member 55 with respect to the actuator plate section 36. This can be accomplished through a slot 59 and a fastener 60 as shown in FIGS. 1 and 2.

In the use of the novel welder's helmet of the present invention as shown in the drawings, the helmet 11 is first placed on the head by a welder. The shield section 17 is positioned in front of the face with the viewing opening 19 adjacent to the eyes and the band section 18 around the top of the head. The welder positions his chin in contact with the chin-contacting member 55 and the helmet is ready for use.

To actuate the filter actuating portion 15 of the helmet 11, the welder moves his chin downwardly. Pressure against the chin-contacting member 55 causes it to move downwardly which in turn moves actuator plate section 36 downwardly. Downward movement of the plate section 36 causes the stud members 37 and 38 extending therefrom to move downwardly in slots 27 and 28 respectively.

Figure 4:
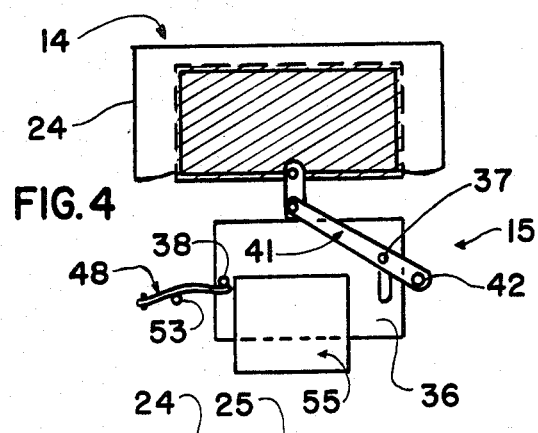
FIG. 4 is a schematic illustration of the reverse side of the filter mechanism shown in FIG. 3 with the filter in a raised position.
Figure 5:
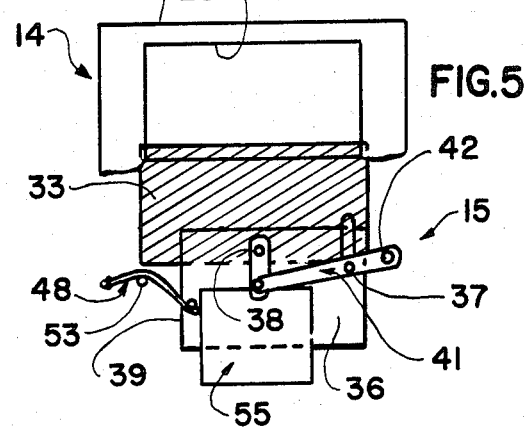
FIG. 5 is a schematic view of the filter mechanism shown in FIG. 4 in a lowered position.

Since stud member 37 is positioned in opening 45 of arm member 41, the arm member moves downwardly about pivotal connection 42. This movement of the arm member 41 moves the link member 43 downwardly and causes the filter member 33 connected thereto to slide downwardly in guides 35. Thus, the filter member 33 is moved from a position over viewing opening 25 in the third frame section 24 as shown in FIG. 4 to a position below the opening as shown in FIG. 5.

Raising the chin to a normal position releases the pressure on chin-contacting member 55. This action allows spring 48 to act on the stud 38 of the actuator plate section 36 drawing it upwardly. The upward movement of the plate section pushes arm member 41 upwardly so that link member 43 will return the filter member 33 to a position over the opening 25 and the viewing opening 19 of the shield section 17.

As the welder goes about his work with his helmet on his head, he can perform his tasks with good visibility while providing protection for his eyes when necessary. This can be accomplished by raising and lowering the movable filter 33 when required without using his hands. The welder can align parts, strike an arc, inspect his work, remove slag from a weld and similar low light intensity tasks with the filter 33 in a lowered position while viewing through fixed filter 34 and safety lens 61. The welder can achieve this result by moving his chin downward and pressing against chin-contacting member 55.

When the welder is actually welding and requires full protection against the intense light which could harm his eyes, he simply raises his chin to a normal position which allows plate section 36 to move upwardly and in turn allows filter 33 to move into the viewing opening 19 so he is viewing through both filters 33 and 34 and lens 61.

The above description and the accompanying drawings show that the present invention provides a novel welder's helmet which permits a filter to be raised and lowered simply and conveniently. The raising and lowering can be accomplished repeatedly during a work day without fatigue or discomfort. Operation of the helmet of the invention can be performed with a normal chin movement. Thus, successful use of the helmet can be learned in a short time. Therefore, a minimum of attention to the operation of the helmet is required.

The welder's helmet of the invention is simple in design and can be manufactured relatively inexpensively. Fabrication of the helmet can be accomplished with commercially available materials and components and semiskilled labor easily and quickly. The helmet is durable in construction and requires little maintenance. Also, the design permits adjustment for different head sizes and shapes.

It will be apparent that various modifications can be made in the particular welder's helmet described in detail above and shown in the drawings within the scope of the invention. For example, the size, configuration and arrangement of components can be changed to meet specific requirements. Also, the shield portion and the head band can be different. The filters can be fabricated from a variety of materials including glass, plastic and the like. Therefore, the scope of the invention is to be limited only by the following claims.

What is claimed is:

1. A welder's helmet including a helmet portion, a filter support portion, a filter portion and a filter actuating portion; said helmet portion including a shield section, a head band section connected to said shield section, a viewing opening in said shield section; said filter support portion being mounted adjacent to said viewing opening, said filter support portion including a first frame section, said first frame section being disposed over the outside of said viewing opening, a second frame section disposed over the inside of said viewing opening, said second frame section including an opening therein adjacent said shield viewing opening, a third frame section disposed adjacent to said second frame section, said third frame section including an opening adjacent said helmet viewing opening, said third frame section including an elongated vertically oriented slot therethrough below said third frame section opening, said filter portion including a filter member slidably positioned between said second and third frame sections, said filter member being movable from a position between said second and third frame section openings to a position below same; said filter actuating portion including an actuator plate section disposed over said third frame section and movable with respect thereto, guide means for said actuator plate section, said actuator plate section being movable linearly in a plane substantially parallel to said third frame section, a stud member extending from one side of said actuator plate section, said stud member being positioned to extend through said elongated opening in said third frame section, an actuator arm member disposed between said second and thrd frame sections, said actuator arm member being pivotally connected to one of said second or third frame sections, said pivotal connection being adjacent one end of said arm member, a link member operatively connecting said filter member with said actuator arm member at a point remote from said pivotally connected end thereof, said stud member of said actuator plate section extending through an opening in said actuator arm member disposed along the length thereof, biasing means urging said filter member into a position over said viewing opening of said shield section, said biasing means including a spring strip operatively connected between said actuator plate section and one of said frame sections, a chin-contacting member affixed to said actuator plate section, said chin-contacting member including a substantially horizontal section and a substantially vertical section; whereby when said helmet is positioned on a person's head, movement of the person's chin while in contact with said chin-contacting member will cause said filter member to move downwardly from said viewing opening.

2. A welder's helmet according to claim 1 wherein said filter portion includes at least one fixed filter member.

3. A welder's helmet according to claim 1 wherein said filter support portion includes a safety lens disposed on the outside of said viewing opening of said shield section.

4. A welder's helmet according to claim 1 wherein at least one of said second or third frame sections includes guide means for said filter member.

5. A welder's helmet according to claim 1 wherein said filter support portion includes a fourth frame section disposed over said third frame section.

6. A welder's helmet according to claim 5 wherein one of said third or fourth frame sections includes guide means for said actuator plate section.

7. A welder's helmet according to claim 1 wherein said chin-contacting member is connected to said actuator plate section through a triangular section extending outwardly from said plate section substantially perpendicular thereto.

8. A welder's helmet according to claim 1 including means for adjusting the position of said chin-contacting member with respect to said actuator plate section.

9. A welder's helmet according to claim 1 wherein said filter support portion includes means for securing said first, second and third frame sections together.

10. A welder's helmet according to claim 9 wherein said securing means includes a plurality of spaced fasteners.

11. A welder's helmet according to claim 1 wherein said viewing opening of said shield section has a generally rectangular configuration.

12. A welder's helmet according to claim 1 wherein said head band section is pivotally connected to said shield section.

* * * * *